(12) United States Patent
Beck et al.

(10) Patent No.: US 8,993,257 B2
(45) Date of Patent: Mar. 31, 2015

(54) SYSTEM AND METHOD FOR STUDYING EPIDERMIS SAMPLES EX VIVO

(71) Applicant: University of Rochester, Rochester, NY (US)

(72) Inventors: Lisa A. Beck, Rochester, NY (US); Anna De Benedetto, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 13/743,879

(22) Filed: Jan. 17, 2013

(65) Prior Publication Data

US 2013/0210055 A1    Aug. 15, 2013

Related U.S. Application Data

(60) Provisional application No. 61/587,236, filed on Jan. 17, 2012.

(51) Int. Cl.
| | |
|---|---|
| C12Q 1/02 | (2006.01) |
| C12M 1/34 | (2006.01) |
| C12M 3/00 | (2006.01) |
| C12N 5/00 | (2006.01) |
| G01N 33/50 | (2006.01) |
| B01L 3/00 | (2006.01) |
| G01N 33/483 | (2006.01) |

(52) U.S. Cl.
CPC .......... *G01N 33/5044* (2013.01); *B01L 3/5085* (2013.01); *B01L 2300/0609* (2013.01); *B01L 2300/0681* (2013.01); *B01L 2300/0829* (2013.01); *G01N 33/4833* (2013.01)
USPC ........................... 435/29; 435/287.1; 435/325

(58) Field of Classification Search
USPC ............................................. 435/325, 287.1
See application file for complete search history.

(56) References Cited

U.S. PATENT DOCUMENTS

| | | | | |
|---|---|---|---|---|
| 4,686,190 A | * | 8/1987 | Cramer et al. | ............. 435/287.1 |
| 2004/0235145 A1 | * | 11/2004 | Cima et al. | ................. 435/287.1 |

OTHER PUBLICATIONS

Scott, E.J. Van, Mechanical separation of the epidermis from the corium. Journal of Investigative Dermatology, vol. 18 (1952) p. 377-379.*
Zewert et al., Transdermal transport of DNA antisense oligonucleotides by electroporation. Biochemical and Biophysical Research Communications, vol. 212, No. 2 (1995) pp. 286-292.*
Segre, J., Epidermal barrier formation and recovery in skin disorders. The Journal of Clinical Investigation, vol. 116, No. 5 (May 1, 2006) pp. 1150-1158.*
Segre, J., "Epidermal Barrier Formation and Recovery in Skin Disorders"; J Clin Invest. May 2006;116(5):1150-8.
Asmar, R., et al., "Host-Dependent Zonulin Secretion Causes the Impairment of the Small Intestine Barrier Function After Bacterial Exposure"; in Gastroenterology, Nov. 2002;123(5):1607-15.

* cited by examiner

*Primary Examiner* — Jon P Weber
*Assistant Examiner* — Kara Johnson
(74) *Attorney, Agent, or Firm* — Laurence J. Hyman; Hyman IP Law

(57) ABSTRACT

An epidermal sample is placed into a sample holder formed as a sandwich assembly. The sample holder is placed in an upper well within a lower well to be exposed to media in both wells. Properties of the sample can be studied, such as paracellular flux, transepidermal electric resistance, reaction to compounds, and epidermal barrier recovery.

23 Claims, 5 Drawing Sheets

SYSTEM AND METHOD FOR STUDYING EPIDERMIS SAMPLES EX VIVO

REFERENCE TO RELATED APPLICATION

The present application claims the benefit of U.S. Provisional Patent Application No. 61/587,236, filed Jan. 17, 2012, whose disclosure is hereby incorporated by reference in its entirety into the present disclosure.

FIELD OF THE INVENTION

The present invention is directed to methods of studying full thickness epidermal samples ex vivo and more particularly to such methods involving separation of the epidermis from the dermis.

DESCRIPTION OF RELATED ART

The skin provides a vital barrier structure that protects vertebrates from both routine and extreme environments, including exposure to antigens, solvents, ultraviolet light, detergents, microorganisms, toxins, nanoparticles, particulate matter, weather conditions (e.g., temperature and humidity) and a variety of other physical insults. In mammalians, the skin has two major components: epidermis (outermost portion above the basement membrane zone) and dermis. In terrestrial vertebrates, the epidermis, where the skin barrier function resides, is highly stratified, as shown in FIG. 1, which is modified from *J Clin Invest.* 2006 May; 116(5): 1150-8. The epidermis 100 has an outermost layer or barrier structure 102 that is cornified (i.e., enucleated compacted cells)—referred to as the stratum corneum. Below that cornified layer, the epidermis has another barrier structure 104 that controls diffusion of water, solutes, macromolecules, and microbes through the paracellular pathway, and this barrier structure is called tight junctions (TJ). TJ are observed by electron micrography at the level of the stratum granulosum 106. Below this, there are two additional layers, namely, the stratum spinosum 108 and the stratum basale 110, the latter of which sits directly on the basement membrane 112.

In vitro, the integrity of epithelial (or endothelial) TJ can be evaluated by one of two complementary, but non-overlapping, functional assessments: 1. Trans-epithelial electric resistance (TEER) measures the resistance to ion flow, and 2. The paracellular flux of macromolecules that typically uses fluorochrome-conjugated probes of different radii to evaluate TJ pore size (or any other conjugation model that would allow quantification of the movement of a particle or macromolecule from one side of the epidermis to the other). To date, those assays can be performed in skin samples only by utilizing a Ussing chamber system that measures the short-circuit current (Isc) and is the measure of net ion transport taking place across the epithelium. However, that system is highly sophisticated (requiring a very skilled technician to run and maintain the system) and is expensive to purchase, operate and maintain. Therefore, it is not too surprising that the system is only actively used at a few major academic centers.

Evaluation of TJ functions as they relate to a specific disease entity or in response to genetic manipulation of a specific gene product has traditionally been performed using a reductionist approach where the epidermis is modeled with a mono- or bilayer of differentiated keratinocytes (KC) grown in culture. Most often this is with primary samples, as many immortalized keratinocytes have alterations in their TJ function, arguably due to the immortalization. To variable extents, those models require prolonged KC cultures that lead to credible scientific concerns that the purported in vivo phenotype might be altered by prolonged culturing or alteration of the micro-environment (e.g., inflammatory mediators, adhesion signals, etc) that occurs as part of the in vitro set up. Additionally, prolonged culture increases concerns about overt and unrecognized microbial contamination. In summary, even under the most ideal situation, those models are recognized as having important differences compared to the in vivo situation in both animals and humans. The use of a keratinocyte monolayer as a model of the epidermis has been highly criticized because that model does not faithfully reproduce human or animal epidermis, which is a complex, multi-layered structure (FIG. 1).

To date, the only in vivo measurement of barrier integrity measures transepidermal water loss (TEWL). TEWL is a measure of water loss from inside-out. It remains unclear whether this reflects barrier defects from the other direction, namely outside-in, which is a critical clinical question. Additionally, it only measures water loss and cannot provide information on the leakiness of the epidermis for macromolecules, microorganisms, drug penetration, etc.

In a separate field of endeavor, a device for ex vivo mammalian intestines and intestinal cell monolayers was introduced by Asmar E. et al. in *Gastroenterology*, 2002 November; 123(5): 1607-15. The device taught therein is not used or usable for skin samples.

The commercially available Snapwell™ (Corning) is utilized for cell cultures, and in this marketed form it is not suitable for studying intact skin samples. As shown in FIG. 2, a Corning Snapwell™ insert 202 includes a detachable ring 204 with a filter 206 for growing cells to confluence.

SUMMARY OF THE INVENTION

It is therefore an object of the invention to provide a simple and inexpensive system and method for studying vertebrate (e.g., mammalian) epidermis samples ex vivo. Vertebrates include the jawless fish, bony fish, sharks and rays, amphibians, reptiles, mammals, and birds.

To achieve the above and other objects, the present invention is directed to systems and methods that enable one to study barrier properties and functions of fully stratified (full thickness) epidermal samples from virtually any vertebrate skin sample, including for example, healthy and diseased human subjects or wild-type and genetically manipulated animal strains. Alternatively, the system could be modified to accommodate 3D epidermal skin equivalents, such as organotypic cultures, raft cultures, commercially available reconstructed skin such as EpiDerm™ (MatTeck Corporation, Ashland Mass.), or inducible pluripotent stem cells matured into epidermal equivalents. Without the technique disclosed herein, such measurements were not a possibility.

The system according to the present invention comprises a first (e.g., upper) well for holding a first medium; a second (e.g., lower) well for holding a second medium; and a sample holder for holding the epidermal sample, the sample holder being positioned to be in contact with the first medium and the second medium, the sample holder comprising: a first plate-layer in contact with the first medium, the first layer having a first hole formed therein to allow the first medium to enter the sample holder; a second layer in contact with the second medium, the second layer having a second hole formed therein to allow the second medium to enter the sample holder; and a filter for holding the epidermal sample, the filter being disposed below the skin samples, between the first layer and the second layer. The sample holder replaces the filter of the conventional Snapwell™ system.

The present invention enables precise measurements of epidermal barrier integrity of fully stratified human and nonhuman epidermis, as well as epidermal equivalents, never before achieved by a variety of arduous, costly and time-consuming primary epithelial cell culture systems, none of which fully recapitulate a fully mature, multilayered epidermis.

The invention will allow measuring epidermal barrier integrity by evaluating transepithelial electric resistance (TEER), using a planar electrode (for example, Endohm-Snap; World Precision Instruments, Sarasota, Fla., USA), and a paracellular flux assay of for example, fluorescently labeled probes of different radii and sizes. Probes can be added to the upper well, and samples will be collected in the lower well over time to determine the paracellular flux. The amount of fluorescent probes that diffuse across the epidermis sample can be measured using an appropriate fluorometer or spectrophotometer.

Another important use of the present invention is to investigate the ex vivo effect of various compounds or culture conditions, including but not limited to drugs/biologics, peptides, lipids, cytokines/inflammatory mediators, toxins, nanoparticles, pH, solutes, temperature, microbial agents/components or their byproducts, UV or other radiation, vehicles or emollients. In each case the effect can be determined when the agent is applied to the upper, lower or both wells. The readouts can be both changes in epidermal barrier function(s) as a static measurement or over time and changes in epidermal gene, protein, metabolome, epigenome expression. The epidermal synthetic changes may be independent of barrier effects or the consequence of barrier effects, and careful kinetic studies will begin to sort the relationship between KC production and barrier functions. This model will provide the ability to assess the importance of directional drug delivery (e.g., whether effects observed on barrier or say inflammation are dependent on the route of exposure, contrasting S. corneum exposure from S. basale [i.e. sub basement membrane] exposure) by applying an agent in either the upper or lower well or both.

Yet another use of the present invention is the study of epidermal barrier recovery. Several human diseases and conditions (e.g. dermatitis, wound, infection, and burn) are characterized by epidermal barrier impairment. Several methods can be adapted to induce epidermal barrier disruption, including but not limited to tape stripping, thermal injury, UV exposure, ionizing radiation and beta-burn. After the injury is performed in vivo or ex vivo, the epidermis can be isolated and placed into the system as previously described. The technology will allow the study of epidermal barrier recovery after the injury allowing for many measurements over time. Additionally, it will be possible to investigate the effect of potential repair substances, including but not limited to drugs/biologics, cytokines, and endogenous as well as exogenous inflammatory mediators (e.g. pattern recognition receptor [PRR] agonists) on epidermal barrier recovery by monitoring recovery of barrier function (e.g. TEER and paracellular flux) and gene or protein expression.

The present invention will also be an ideal system to evaluate the pharmacology and toxicology of systemic and topical drugs/biologics, additives found in both prescription and OTC preparations and cosmeceuticals, environmental toxins, etc. The present invention will allow studying the barrier properties of skin samples in virtually any hospital-based laboratory, academic or biotech/pharmaceutical laboratory.

The methods disclosed herein, in at least some embodiments, involve isolating epidermis samples from in vivo or ex vivo skin tissue. Essentially, the system of the present invention can then be modified to accommodate the specific skin samples (e.g., size, type of experiments, membrane).

The present invention will allow testing various compounds on intact or wounded human and nonhuman skin/epidermis from both discarded skin samples and from subjects with specific diseases or disease states or subphenotypes that might affect epidermal barrier and allow their comparison to healthy subjects. Similarly, that approach can be used for all vertebrates (e.g., rodents, fish, birds, reptiles, amphibians, etc.) as well. Additionally, epidermal equivalents can be tested using the present invention.

BRIEF DESCRIPTION OF THE DRAWINGS

Preferred embodiments of the present invention will be set forth in detail with reference to the drawings, in which.

DETAILED DESCRIPTION OF THE PREFERRED EMBODIMENTS

Figure 1:
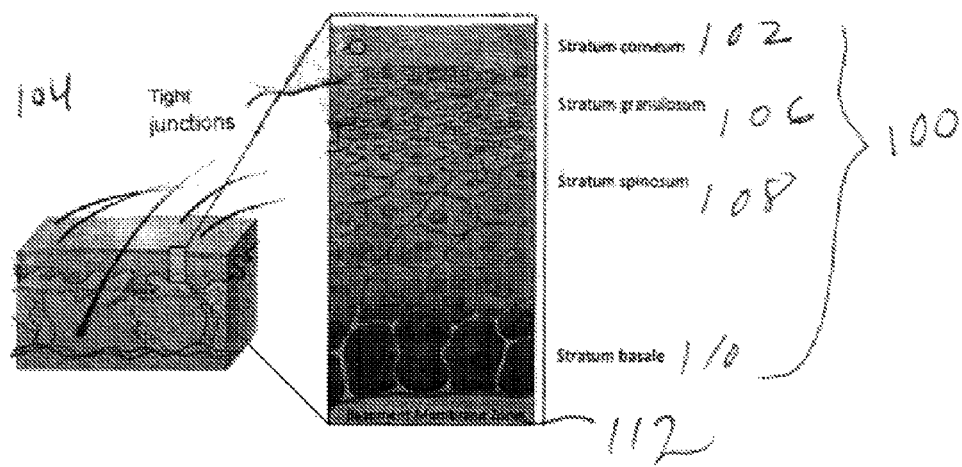
FIG. 1 is a sectional diagram showing the various layers of the epidermis.
Figure 2:
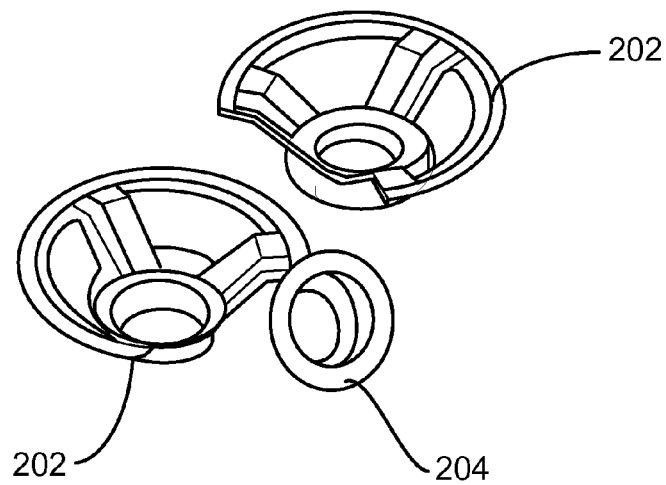
FIG. 2 shows components of the conventional Corning Snapwell™ system.

Preferred embodiments of the invention will be set forth in detail with reference to the drawings, in which like reference numerals refer to like elements or steps throughout.

Figure 3A:
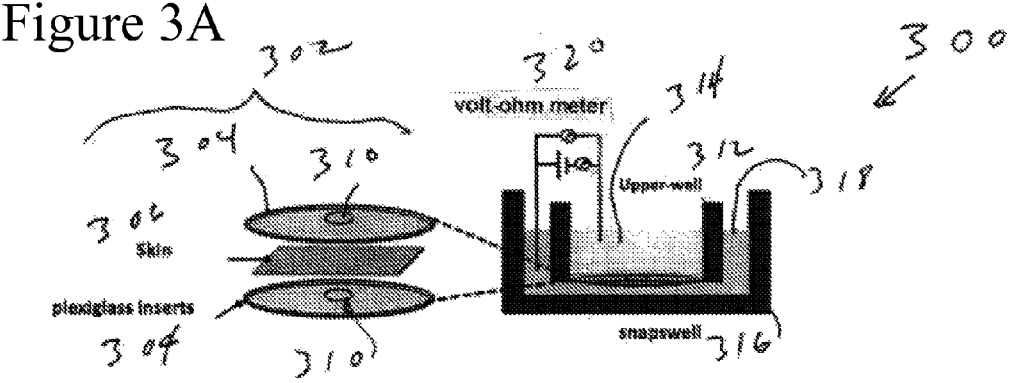
FIGS. 3A and 3B are schematic diagrams of a system in which any of the preferred embodiments can be implemented.
Figure 3B:
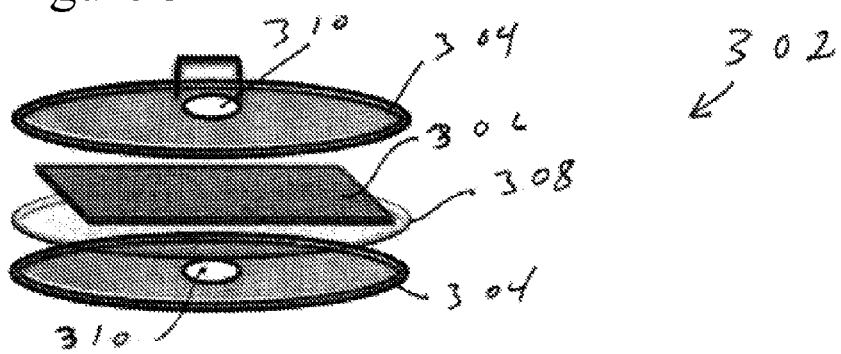

FIGS. 3A and 3B are schematic representations showing the device 300 used in the preferred embodiments. The filter 206 of the original detachable ring 204 in the Snapwell™ (Corning, 3407) is replaced by a sandwich system 302 having two Plexiglas (or any other suitable material) inserts 304, with the epidermis/skin sample 306 lying in between them on a filter paper 308 (Nucleopore Track-etched, #110407; 13 mm diameter & pore: 0.4 µm) so that it covers the opening. The skin sample 306 is inserted with epidermis side up. Each of the inserts 304 has a hole 310 formed therein with a diameter of 0.3 cm and an area of 0.0707 $cm^2$. As in the conventional Snapwell™ system, the sandwich system is 302 is placed between an upper well 312 having a medium 314 and a lower well 316 having a medium 318. A volt-ohm meter 320 is connected between the two media. A 6-well plate or other support can be used for the assay, as is known in the art. Possible modifications to this set up include changing the composition of the inserts (for example—positively or negatively charged plastic polymers or inserts coated with extracellular matrix proteins) or changing the pore configuration and/or dimensions.

The use of the device of FIGS. 3A and 3B will now be disclosed. First, the epidermis samples must be separated from the dermis. Several methods of doing so will be disclosed. The specific method will vary depending of the specific assay or function tested, the source of the epidermis and the question being asked. Methods that can be used to separate the epidermis from the dermis at the basement membrane zone include, but are not limited to:

1. Incubation in dispase (as an illustrative rather than limiting example, 25 caseinolytic units/ml in buffer) for 1.5 h-3 h at 37° C., in which, after incubation, the epidermis can be separated from the dermis using tweezers, and the epidermis sample can be placed in the system;

2. Incubation in 1M NaCl, in which, after incubation, the epidermis can be separated from the dermis using tweezers;

3. Incubation in ammonium thiocyanate, and removing the epidermis with tweezers/forcipes; and 4. Formation of a suction blister, in which an NP-2 negative pressure vacuum apparatus (Electronic Diversities, Finksburg, Md., USA) or other similar apparatus can be applied to a flat skin surface (e.g., volar forearm, back, belly). The blisters are created through the use of suction chambers that are attached to the subjects or animal skin. The blister roof, which consists of full thickness epidermis, can be removed using a sterile (or not) technique and placed in a buffer.

Figure 4:
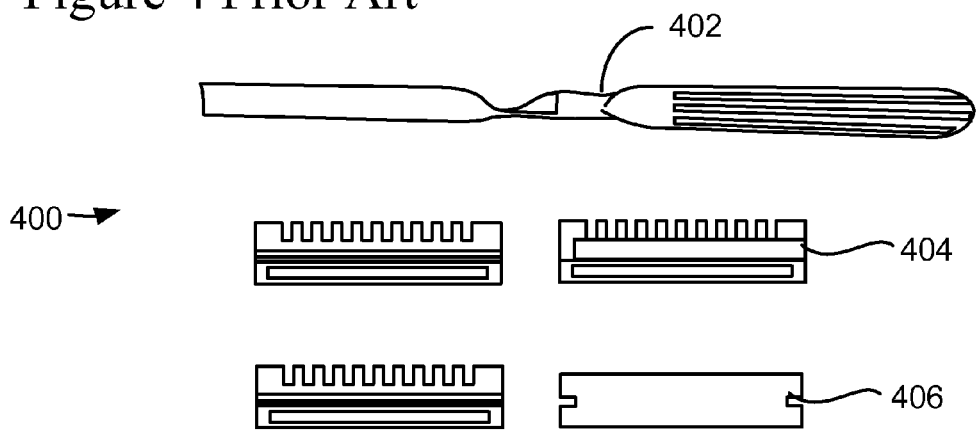
FIG. 4 shows a Weck blade.

Methods that can be used to separate the epidermis from dermis below the Basement Membrane Zone include, but are not limited to, a sterile Weck blade (Goulin Guard). FIG. 4 shows a Weck blade 400, including a handle 402 and interchangeable guards 404 (0.08, 0.010 or 0.012 inch) and blades 406. That method can be used for virtually any vertebrate discarded skin tissue samples or prospectively from well-characterized donors. That enables one to prospectively obtain full thickness skin samples from any body surface in well-characterized individuals. Some examples of where that might be useful would be to understand barrier changes over the natural course of disease development or as function of disease severity, environmental perturbations, disease sub-phenotypes, treatment, as a function of host genotype, etc.

The Weck blade is held at a 30-45° angle from the donor skin (e.g. living subject or discarded skins from plastic surgery procedures) surface, while a gentle traction behind the blade is provided by the other hand. Using different depths (e.g. 0.08-0.012 inch), based on the skin sample source (e.g. based on differences in epidermal depth in different anatomical areas as well as species-specific differences), we can effectively isolate intact, full thickness epidermal samples with minimal to no dermis (e.g. subepithelial tissue). The epidermis is removed using that Weck surgical blade, cut into smaller samples to fit the apparatus and placed in a calcium-containing buffer until it is mounted in the device.

For very thin skin samples isolated from rodents or other small mammalians, curettage along the dermal surface of the biopsy can be performed with a blade to minimize the amount of dermis taken. Alternatively, skin can be incubated in ammonium thiocyanate and epidermis removed from dermis. Murine skin can be isolated from any anatomical area, defatted using a surgical blade, cut into smaller samples to mount in the apparatus.

Epidermal samples are then inserted into the system. Once the skin samples are mounted into the system, the samples can be tested immediately and for as long as the epidermal sample remains viable, which depends on a number of factors but is typically upwards of 48 hrs if incubated underphysiological conditions. Using this model, one can start with healthy control epidermis samples and study the effect of changes in temperature, osmolarity, pH, microbial organisms and/or by products, solutes, particulates, radiation, on barrier function to give just a few examples. Media can be added to both wells or only to the lower well.

Based on the skin samples to analyze and the specific assay to perform, numerous modifications can be considered to better adapt the system. Such modifications include but are not limited to: size of the chamber; size, thickness, composition, coating/surface charge of the inserts; size and shape of the inserts' internal hole; and material and permeability of the filter.

We have tested the invention using human discarded skin as well as murine epidermal samples. Several examples of the invention applications are reported hereafter.

Figure 5:
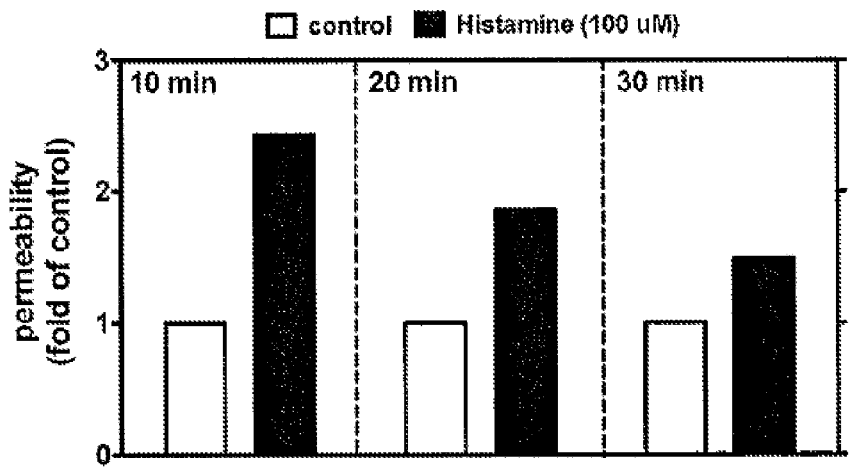
FIG. 5 is a graph showing a measured change in paracellular flux after histamine treatment.

We have tested the effect of Histamine on intact human epidermis samples and found it can reduce epidermal barrier function. FIG. 5 shows a graph of the results. Human skin epidermal samples were isolated with dispase treatment and mounted into the system, and the paracellular flux of fluorescein was evaluated at 10, 20 and 30 minutes. Histamine 100 µM enhanced the paracellular flux of fluorescein, indicating greater leakiness of the epidermal sample in response to exposure to histamine.

Figure 6:
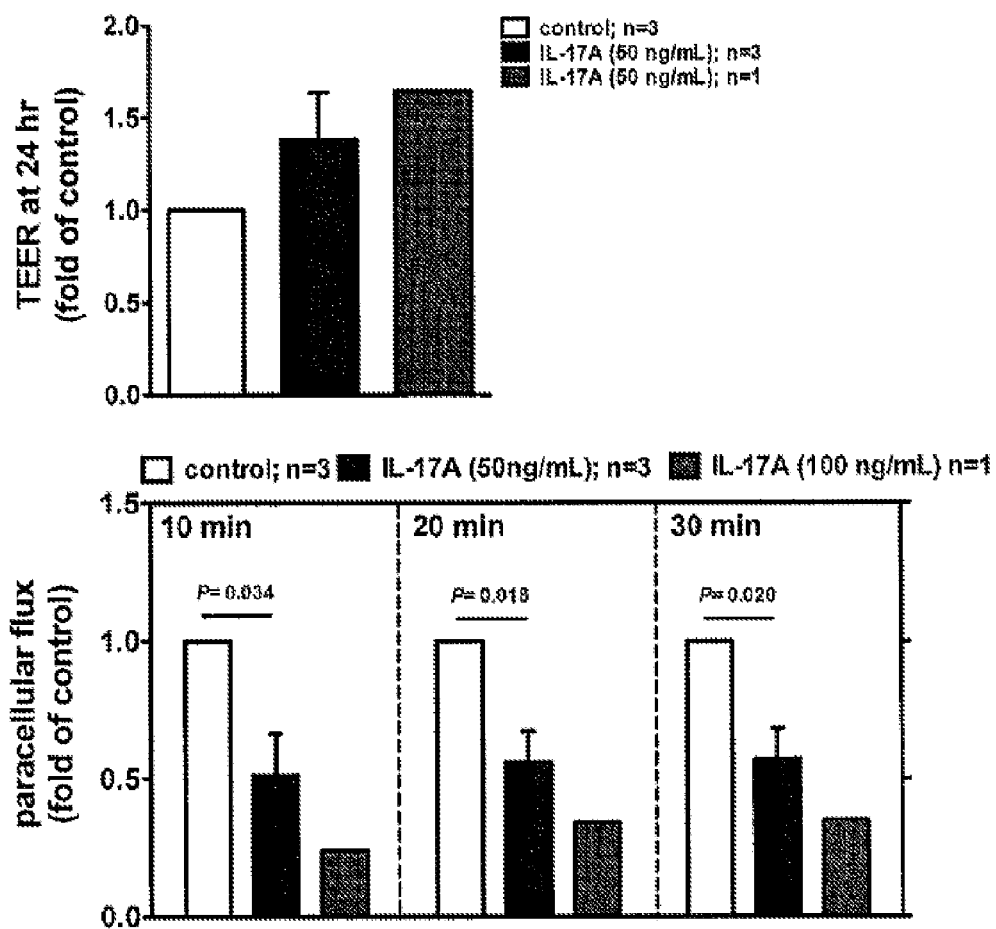
FIG. 6 is a set of graphs showing a quantification of epidermal barrier enhancement after treatment with IL17A.
Figure 7:
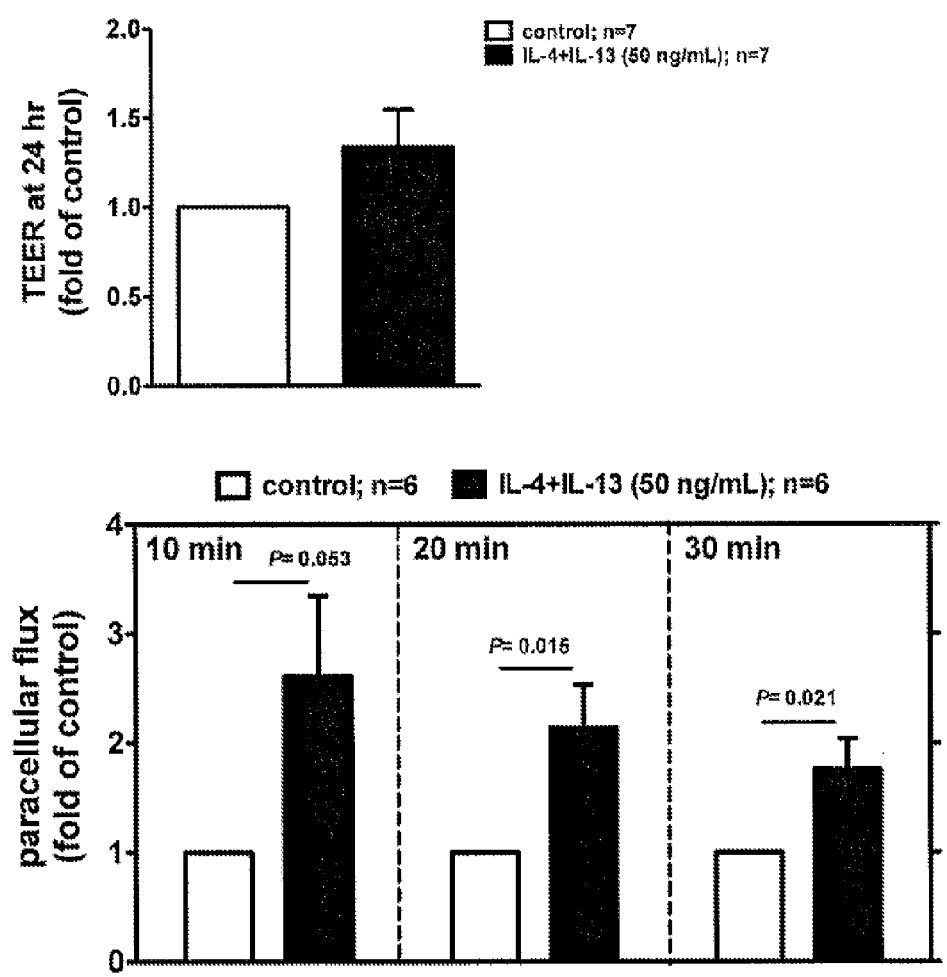
FIG. 7 is a set of graphs showing a quantification of epidermal barrier disruption in human skin samples after treatment with Th2 cytokines.

We have also used the invention to test the effect of cytokines relevant to human disease on epidermal barrier function recovery. Human discarded skin was tape stripped to induce a barrier impairment, this barrier-disrupted epidermis was isolated using the Weck blade and placed into the system. Samples were than treated for 24 h with human recombinant IL17A, a prototypic cytokine commonly found within the skin lesions of psoriasis (FIG. 6) or the Th2 cytokines, IL4 and IL13, commonly found in atopic dermatitis (FIG. 7). After 24 h treatment with human recombinant IL17A (50 and 100 ng/ml), TEER was increased, and paracellular flux was reduced as compared with a sample treated with media alone. Those data indicated IL17A enhanced epidermal barrier recovery.

When we treated epidermal skin samples with human recombinant IL4 (50 ng/ml) and IL13 (50 ng/ml), TEER was reduced, and paracellular flux was increased as compared with a sample treated with media alone, suggesting weakened barrier function.

Figure 8:
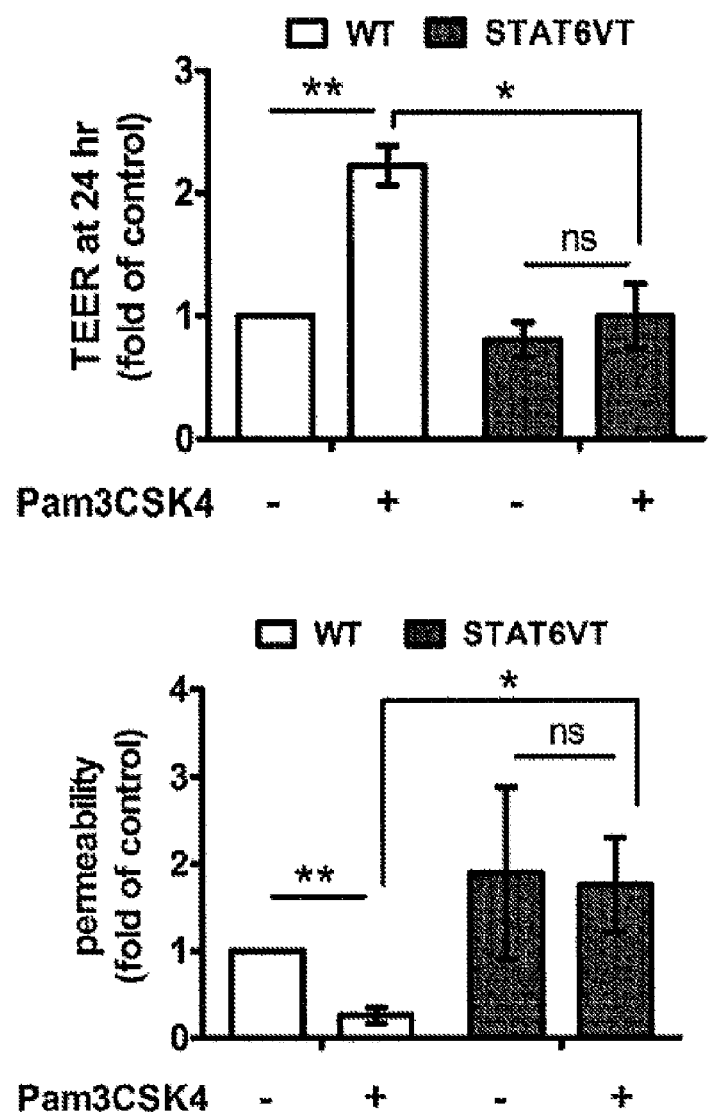
FIG. 8 is a set of graphs showing a comparison of epidermal barrier recovery among genetically modified mouse strains and also showing the effects of a compound on barrier recovery.

We have also used the present invention in a murine model. Skin barrier recovery after in vivo tape stripping was evaluated in wild type mice as compared to genetically modified mice that expressed a constitutively activated form of STAT6 under the CD2 locus, that results in the enhanced expression of Th2 cytokines (IL-4 and IL-13). Skin samples were collected from the healthy, nonperturbed skin of the back or from an area of the back that underwent tape stripping. The dermis was removed by scraping with a surgical blade and skin samples were mounted in the system. We observed no differences in recovery between the two mice strains. However, when we treated both samples with a TLR2 agonist (Pam3CSK4, 10 µM) we noticed a greater recovery in wild type mice as it compared to STAT6 mice. FIG. 8 shows the results. All data are normalized to WT vehicle control group. In FIG. 8, ns: not significant; *$P<0.05$, $P<0.01$, *$P<0.001$. (WT, n=3; STAT6VT, n=3). This suggested that these hyper Th2 mice (e.g. STAT6 mice) had developed a defect in TLR2 signaling such that they no longer had the expected TJ barrier recovery response to TLR2 ligands.

While preferred embodiments have been disclosed in detail above, those skilled in the art who have reviewed the present disclosure will readily appreciate that other embodiments can be realized within the scope of the invention. For example, disclosures of specific numerical quantities and ranges are illustrative, as are disclosures of specific materials, as those skilled in the art will understand the ways in which the present invention can be adapted to a variety of needs. Also, other techniques for obtaining an epidermal sample can be used. Therefore, the present invention should be construed as limited only by the appended claims.

What is claimed is:

1. A system for studying an epidermal sample ex vivo, the system comprising:
   a first well for holding a first medium;
   a second well for holding a second medium; and
   a separable sample holder for supporting the epidermal/skin sample, the sample holder, when the system is in use, being positioned to be in contact with the first medium and the second medium, the sample holder comprising:
   a first layer in contact with the first medium, the first layer having a first hole formed therein to allow the first medium to enter the sample holder;
   a second layer in contact with the second medium, the second layer having a second hole formed therein to allow the second medium to enter the sample holder; and
   a filter for supporting the epidermal sample, the filter being disposed between the first layer and the second layer.

2. The system of claim 1, further comprising an electrical meter connected between the first medium and the second medium.

3. The system of claim 2, wherein the electrical meter comprises a volt-ohm meter.

4. The system of claim 1, wherein the first well is disposed within the second well.

5. The system of claim 1, wherein the first well, the second well, the first layer, the second layer, and the filter are configured to be separable.

6. A method for studying an epidermal sample ex vivo, the method comprising:
   (a) providing a system comprising:
      a separable sample holder for supporting the epidermal/skin sample, the sample holder, when the system is in use, being positioned to be in contact with the first medium and the second medium, the sample holder comprising:
      a first layer in contact with the first medium, the first layer having a first hole formed therein to allow the first medium to enter the sample holder;
      a second layer in contact with the second medium, the second layer having a second hole formed therein to allow the second medium to enter the sample holder; and
      a filter for supporting the epidermal sample, the filter being disposed between the first layer and the second layer;
   (b) obtaining the epidermal sample;
   (c) placing the epidermal sample into the sample holder and assembling the system; and
   (d) performing a study on the epidermal sample.

7. The method of claim 6, wherein step (c) comprises connecting an electrical meter between the first medium and the second medium.

8. The method of claim 7, wherein the electrical meter comprises a volt-ohm meter.

9. The method of claim 6, wherein the first well is disposed within the second well.

10. The method of claim 6, wherein the first well, the second well, the first layer, the second layer, and the filter are configured to be separable.

11. The method of claim 6, wherein step (b) comprises:
    (i) incubating a skin sample comprising both epidermis and dermis to loosen the epidermis from the dermis; and
    (ii) removing the epidermis from the dermis.

12. The method of claim 11, wherein step (b)(i) is performed using at least one of dispase, NaC1, and ammonium thiocyanate.

13. The method of claim 11, wherein step (b)(ii) is performed mechanically.

14. The method of claim 6, wherein step (b) comprises forming a suction blister.

15. The method of claim 6, wherein step (b) is performed with a blade.

16. The method of claim 15, wherein the blade is a Weck blade.

17. The method of claim 6, wherein step (d) comprises measuring paracellular flux of a fluorescent or similarly tagged substance.

18. The method of claim 17, wherein the fluorescent substance comprises fluorescein.

19. The method of claim 6, wherein step (d) comprises measuring transepithelial electric resistance.

20. The method of claim 19, wherein the transepithelial electric resistance is measured using a planar electrode.

21. The method of claim 6, wherein step (d) comprises studying an effect of a compound on the epidermal sample.

22. The method of claim 21, wherein the compound is introduced into either or both of the first medium and the second medium.

23. The method of claim 6, wherein step (d) comprises studying epidermal barrier recovery.

* * * * *